United States Patent [19]

Haindl et al.

[11] Patent Number: 4,871,356
[45] Date of Patent: Oct. 3, 1989

[54] CATHETER DEVICE

[75] Inventors: Hans Haindl, Melsungen; Jürgen Fuchs, Emstal-Sand, both of Fed. Rep. of Germany

[73] Assignee: B. Braun Melsungen AG, Melsungen, Fed. Rep. of Germany

[21] Appl. No.: 195,112

[22] Filed: May 17, 1988

[30] Foreign Application Priority Data

Jun. 27, 1987 [DE] Fed. Rep. of Germany ....... 3721299
Jan. 20, 1988 [EP] European Pat. Off. ........ 88100702.5

[51] Int. Cl.$^4$ ........................................ A61M 5/00
[52] U.S. Cl. .................................... 604/247; 604/280
[58] Field of Search ............... 604/280, 93, 247, 246, 604/249, 164, 264, 256; 137/853, 859, 860

[56] References Cited

U.S. PATENT DOCUMENTS

| 396,754 | 1/1889 | Mayfield | 604/256 |
|---|---|---|---|
| 1,926,608 | 9/1933 | Ziegler | 604/256 |
| 3,802,433 | 4/1974 | Raven | 604/283 |
| 4,666,429 | 5/1987 | Stone | 604/287 |
| 4,759,752 | 7/1988 | Stober | 604/9 |

FOREIGN PATENT DOCUMENTS 3326648 2/1986 Fed. Rep. of Germany .

Primary Examiner—Stephen C. Pellegrino
Attorney, Agent, or Firm—Spensley Horn Jubas & Lubitz

[57] ABSTRACT

A retentive catheter having a cannula tube through which medications may be injected into a patient. A mandrin may be left in the retentive catheter during the injection. The medication is injected through an injection port and flows through a fluid channel between the mandrin and the cannula tube and is discharged from the cannula tube through a valve. The valve may be of the nonreturn type. The mandril tip prevents blood components from entering into the cannula tube. The protection against contamination is increased because the mandrin need not be removed from a proposed injection.

12 Claims, 4 Drawing Sheets

CATHETER DEVICE

BACKGROUND OF THE INVENTION

1. Field of the Invention

The invention relates to a catheter device and, in particular, to a catheter device comprising a retentive catheter or short catheter.

2. Description of Related Art

There have been known short catheters comprising a cannula tube adapted to be introduced into the vein of a patient's arm while the connector at the rear end of the cannula tube is fixed to said arm. In the vicinity of the connector, there is provided an injection port through which fluid drugs may be administered to the patient.

The catheter device comprises a mandrin which is inserted through the connector into the cannula tube to block the cannula tube if no injection of medication or no infusion is made. If no injection is made through the catheter, the mandrin ensures that blood components are prevented from penetrating into the catheter and causing a thrombus formation. Further, the mandrin ensures that no contaminations may penetrate into the catheter and from there into the body of the patient.

The known short catheters are unsatisfactory because, prior to each injection, the mandrin must be removed in order to open the connection from the injection port to the cannula tube and to unblock the cannula tube. Upon termination of the injection, a sterilized new mandrin has to be introduced. In practice, the mandrin inserted is frequently the same as that removed from the retentive catheter prior to the injection. As evident, such handling is accompanied by a high risk of contamination. Moreover, such manipulations with the mandrin or mandrins are rather complicated for the user.

There has been known a catheter wherein the tube comprises a nonreturn valve at the proximal front end (German Patent No. 35 40 949). The valve stationarily mounted at the catheter tube is opened due to overpressure, but may not be used with an introduced mandrin.

SUMMARY OF THE INVENTION

It is an object of the present invention to provide a catheter device in which the risk of contamination and thrombus formation due to the cannula tube is avoided.

According to a preferred embodiment of the present invention, the mandrin and the cannula tube at the proximal end cooperate as a valve while, with the presence of the mandrin in the catheter, a fluid channel extends from the injection port to the valve. By this means, medications may be injected through the port even in the case of the presence of the mandrin in the catheter. Thus, for injecting medications, the mandrin need not be removed from the catheter but it may stay there permanently. On the other hand, the mandrin is an independent element which need not be introduced before the catheter is applied so that the catheter may be inserted on a metallic puncture cannula into the body of the patient. Upon the introduction of the catheter, the puncture cannula is removed and the mandrin is introduced into it. Hence, the catheter lumen is not blocked by fixed elements.

The invention particularly lends itself to short catheters used as retentive catheters and having a flexible cannula tube of a length of about four to five cm.

The invention offers an advantage in that the mandrin need be introduced only once and may remain in the retentive catheter in the case of repeated injections. If no injection is made, the blocked valve avoids a penetration of blood components into the cannula tube, thus excluding the risk of thrombosing of the cannula tube. Further, the mandrin maintained in the cannula tube acts as a protection against contamination because its rear connector closes the cannula channel against the environment and because, once introduced into the retentive catheter, the mandrin need not be removed any more.

In one embodiment of the present invention a fluid channel is formed between the mandrin and the cannula tube, thus enabling the medication to reach the valve against a low flow resistance. Preferably, the valve is of the type that is opened at low overpressure, and through which the drug is administered into the body of the patient. Said nonreturn valve is also formed by the mandrin and the catheter tube at the front end of the cannula tube. The mandrin should extend at least as far as to the front end of the catheter tube, but it may also slightly project out of the catheter tube.

Another embodiment of the present invention provides a fluid channel extending inside the hollow mandrin, whose front end forms the valve. In this embodiment, the injection port may be provided laterally, in the usual manner, at the connector of the catheter. However, it may be also provided at the rear end of the mandrin, thus allowing injections or infusions through the mandrin over its total length. In this case, no injection port at the retentive cannula is required at all.

According to this embodiment of the invention, the mandrin seals the fluid channel by a valve at the proximal end, thus inhibiting the flow of blood components into the cannula tube. With the use of a nonreturn valve, the shape of the cannula tube end or mandrin end is changed under the pressure of the injected medication which may escape accordingly. However, a sharp drug jet is avoided.

There are at least two possibilities for the operation of the nonreturn valve; it may be opened by radial deformation of the catheter tube or the mandrin or by the axial stretching of the mandrin under the injection pressure.

The valve may be of the type operated mechanically and whose condition is changed by moving the mandrin. In this case, no fluid pressure is required to open the valve so that the catheter device comprising a manually adjustable valve, may be also used for gravity infusion in which only a low fluid pressure is available.

BRIEF DESCRIPTION OF THE DRAWINGS

Embodiments of the invention will be explained hereinafter in more detail with reference to the drawings in which.

DESCRIPTION OF THE PREFERRED EMBODIMENT

Figure 1:
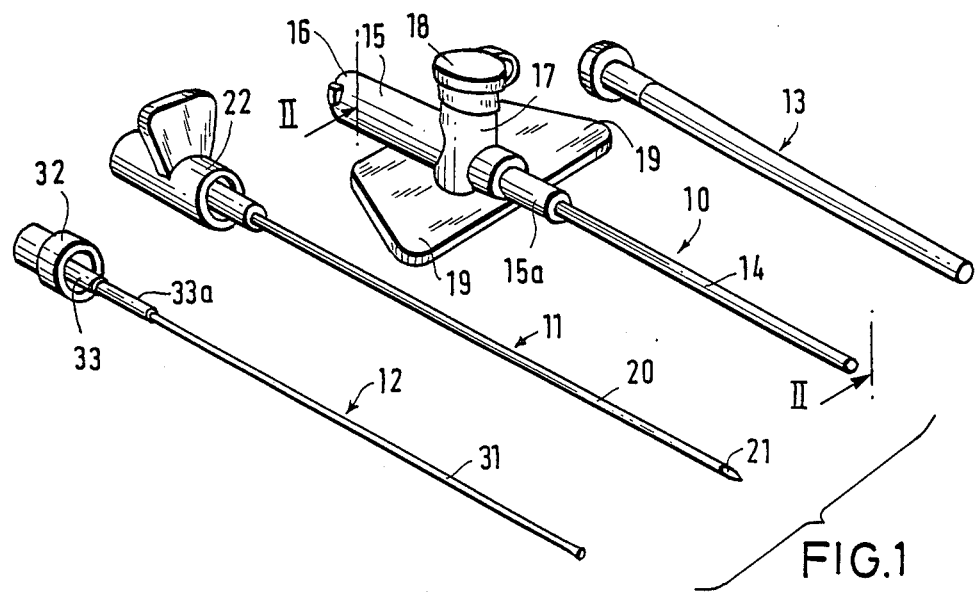
FIG. 1 shows the individual elements of a complete catheter set.

The following detailed description is of the best presently contemplated mode of carrying out the invention. This description is not to be taken in a limiting sense, but is made merely for the purpose of illustrating the general principles of the invention. The scope of the invention is best defined by the appended claims.

The retentive catheter 10 contains a straight, elongated, flexible, plastic cannula tube 14 which is about four to five cm long. The rear end of the cannula tube 14 is provided with the connector 15 having a connecting adapter 16 and a lateral injection port 17. The channel of the connecting adapter 16 is axially aligned with that of the cannula tube 14. The injection port 17 comprises a detachable sealing cap 18 which may be removed in order to connect to the port 17 a syringe or another fluid source. Further, the connector 15 includes laterally projecting wings 19 by which the retentive catheter 10 may be fixed on the patient's skin to which they are adhesively bonded for instance by plaster, while the cannula tube flatly extends through the skin into a vein.

The puncture cannula 11 comprises a metallic tube 20 whose front end is provided with a ground section 21 for piercing the skin. The rear end of the cannula includes a connector 22 cooperating with the connecting adapter 16 and adapted to be locked therewith. The connecting adapter 16 and connector 22 form a Luer-lock-connection allowing to rotatingly screw together both elements to sealingly connect them accordingly. If connector 22 is seated on connecting adapter 16, tube 20 extends through the connecting adapter 16 and through the cannula tube 14, whereby the tube tip with the ground section 21 projects out of the cannula tube 14. In this condition, puncture may be carried out in that the tube 20 closely embraced by cannula tube 14 is inserted into the vein. Upon the puncture of the vein, the puncture cannula 11 is removed from the retentive catheter 10 and the latter is fixed on the patient's skin. Subsequently, mandrin 12 is inserted through the connecting adapter 16 into the retentive catheter 10, said mandrin 12 comprising an elongated rod 31 carrying at its rear end a connector 32 which may be sealingly locked with the connecting adapter 16. If connector 32 is seated on adapter 16, the front end of rod 31 extends as far as to the front end of the cannula tube 14. Between connector 32 and rod 31, there is a stiffening zone 33a which is connected to the core 33 of the connector 32 being designed as a female Luer-cone.

In packaged condition of the catheter set, tube 20 of the puncture cannula 11 is inserted into the retentive catheter 10, and the protective cap 13 is slipped over the cannula tube 14 thus covering the ground section 21. The rear end of the protective cap 13 is clampingly retained on an attachment 15a of the connector 15. All of the elements of the catheter set are sterilized and accommodated in a germ-free package.

Figure 2:
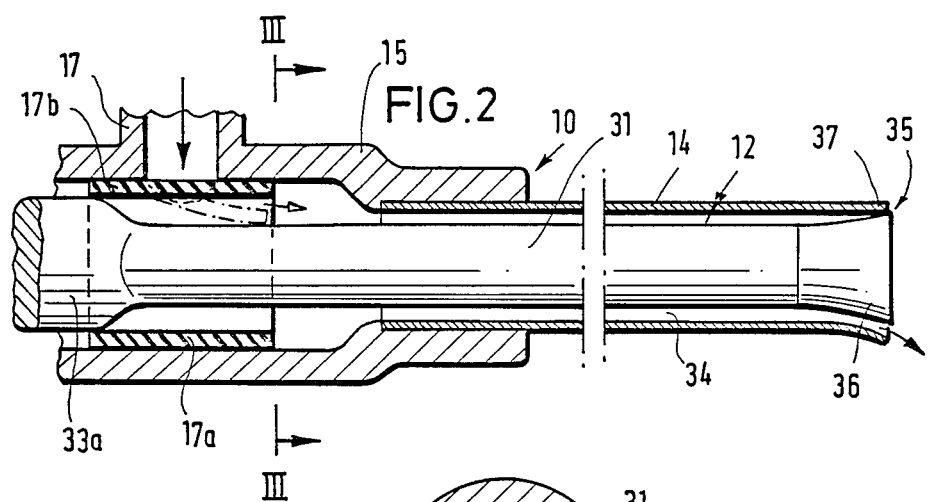
FIG. 2 is a section of the retentive catheter along line II—II of FIG. 1.
Figure 3:
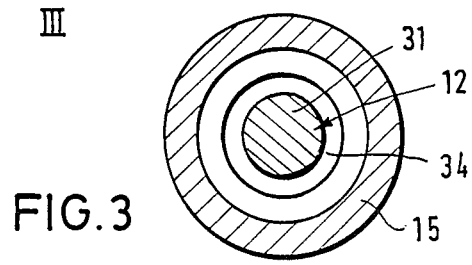
FIG. 3 is a cross section along line III—III of FIG. 2 in a first embodiment of the catheter device.

FIGS. 2 and 3 show a first embodiment comprising rod 31 of the mandrin 12 having a circular cross section and a diameter of such a small dimension that an annular fluid channel 34 extends between the inner lumen of the cannula tube 14 and mandrin 13, said fluid channel 34 connecting the injection port 17 to the nonreturn valve 35 provided at the catheter front end, said nonreturn valve 35 of this embodiment consisting of a headpiece 36 having a flaring cross section at the front end of rod 31 and of the radially expandable end section 37 of the cannula tube 14. If no injection is made, the end section 37 embraces the head piece 36. However, during an injection, the nonreturn valve is opened in that the end section 37 is expanded and lifted from the headpiece 36. By this means, an annular outlet is formed. The upper half of FIG. 2 shows the closing position, the lower half the opening position of the nonreturn valve 35.

The stiffening zone 33a of the mandrin 12 has a rectangular cross section which does not fill up the fluid channel 34 inside the connector 15, thus ensuring a lateral flow around the stiffening zone 33a which further allows the inflow of fluid from the injection port 17 into the fluid channel 34. A hose portion 17a whose rear end 17b is adhesively bonded to the wall of connector 15 is provided in the area of the connector 15 in which ends the injection port 17, while the circumference of the hose portion loosely adjoins the inner wall of the connector 15. The hose portion 17a forms a valve separating the injection port 17 from the interior of the connector 15 and being opened by the fluid pressure in the injection port 17.

If no fluid is injected through the injection port 17, the nonreturn valve 35 is closed so that no blood components may penetrate into the cannula tube 14. The nonreturn valve 35 is only opened under pressure inside the cannula tube 14 if said pressure is superior to the vein pressure. The mandrin 12 is also maintained in the retentive catheter in times of no injection.

Figure 4:
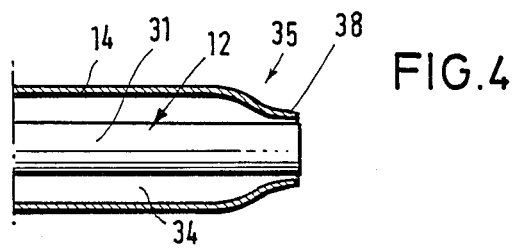
FIG. 4 is a longitudinal section of a second embodiment of the nonreturn valve.

The front end of the cannula tube 14 of the embodiment of FIG. 4 has a constricted range 38 in which the inner diameter of the cannula tube is reduced to the outer diameter of the mandrin 12 to obtain a blocking of the fluid channel 34 at the front end. The constricted range 38 is flexibly expandable, for instance by reducing the material thickness to permit to overcome the fluid barrier by the injection pressure.

Figure 6:
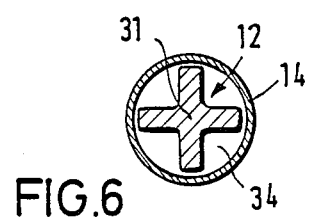
FIG. 6 is a cross section along line VI—VI of FIG. 5.
Figure 5:
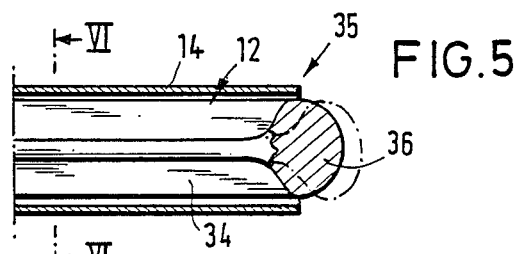
FIG. 5 is a longitudinal section of a third embodiment of the nonreturn valve.

The embodiment of FIGS. 5 and 6 shows the design of the shaft 31 whose periphery adjoins the inner wall of the cannula tube 14, but its cross section does not fill up the cannula tube. This is achieved by a shaft cross section in the shape of a cross. The front end of the mandrin 12 is provided with a headpiece 36 which fills up the total cross section of the cannula tube 14 and slightly projects from the latter. If a drug is injected, the headpiece is advanced by the injection pressure so that it leaves the interior of the cannula tube 14, and the drug may exit from the fluid channel 34. The elongation of the mandrin 13 for opening the nonreturn valve 35 is about 0.5 mm.

Figure 7:
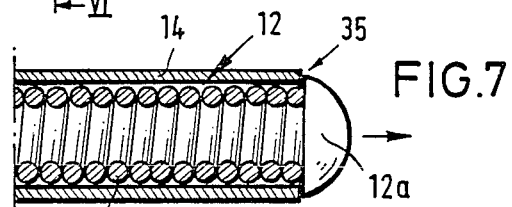
FIG. 7 is a longitudinal section of an embodiment comprising a helical mandrin.

The mandrin shown in FIG. 7 consists of a helical coil 39 of a plurality of windings of metal or plastic, which, at their proximal end, are closed by welding or fusing with a headpiece 12a which sealingly adjoins the front end within the coil 39. Due to the injection pressure, the coil 39 is expanded with a resultant elongation of the mandrin 12 and a lifting of the headpiece 12a from the end of the cannula tube 14. At the same time, the windings of the coil previously tightly juxtaposed, spread away from each other.

Figure 8:
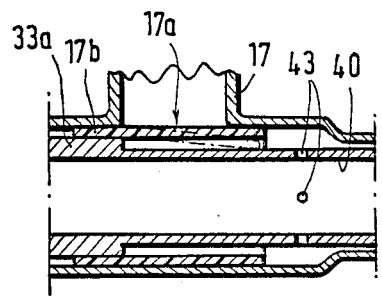
FIG. 8 is a longitudinal section of an embodiment comprising a hollow mandrin.
Figure 8:
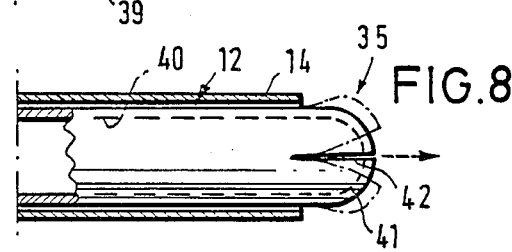

FIG. 8 shows a mandrin 12 which is hollow and which contains a longitudinal fluid channel 40. The external diameter of mandrin 12 substantially corresponds to the inner diameter of the cannula tube 14, while the front end 41 of the mandrin 12 projects out of the cannula tube 14, said front end 41 forming the nonreturn valve 35 being provided with one or more transverse slots 42 which subdivide the front end 41 into two halves or a number of segments which, like a fish-mouth valve, radially evade under internal pressure to open in opposite directions. The fluid channel 40 communicates with the injection port 17 via radial holes 43 in the mandrin wall. The cross section of the thicker stiffening area 33a of this embodiment is round and sealingly rests against the rear end 17b of the hose portion 17a while the front region of the hose portion 17a is deformable inwardly.

Figure 10:
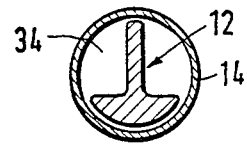
FIG. 10 is a cross section along line X—X of FIG. 9.
Figure 9:
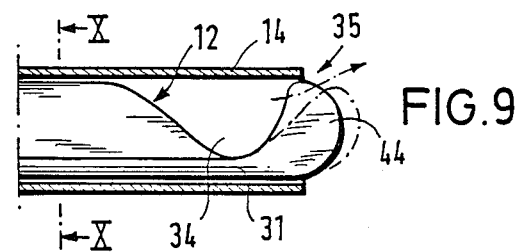
FIG. 9 is a longitudinal section of an embodiment comprising a flexibly movable head portion of the mandrin.

FIGS. 9 and 10 show an embodiment in which the cross section of the mandrin 12 is substantially T-shaped so that space for the fluid channel 34 is available inside the cannula tube 14. The nonreturn valve 35 consists of a flexible headpiece 44 projecting out of the end of the cannula tube 14 which end is normally closed by it.

Due to an injection pressure in the fluid channel 34, the headpiece 44 connected over only a part of its periphery to the rod 31, yields as indicated by the dash-dotted line in FIG. 9. By the flexible radial yielding of the headpiece 44, a passage is opened at the end of the cannula tube 14.

Figure 11:
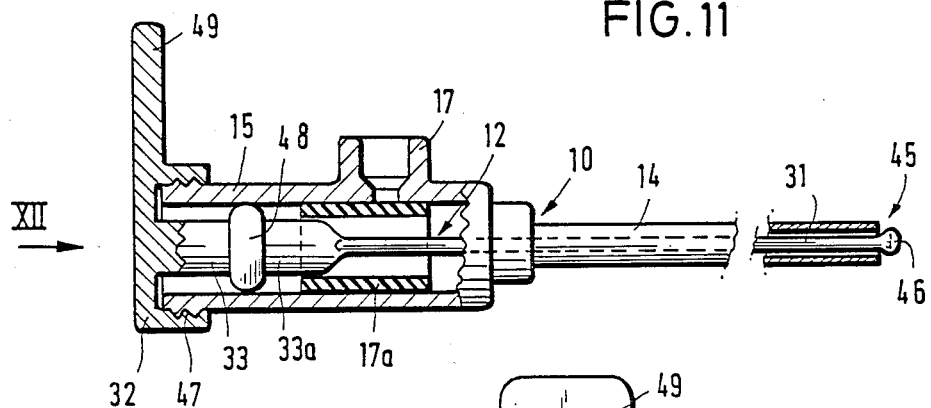
FIG. 11 shows an embodiment in which the valve at the front end of the cannula tube is operated by rotating the mandrin.
Figure 12:
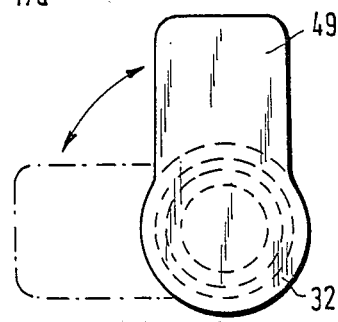
FIG. 12 is a view of the device of FIG. 11 from the direction of arrow XII.

As evident from FIGS. 11 and 12, the front end of the mandrin 12 has a thicker headpiece 46 which, if the mandrin is withdrawn, locks the front end of the cannula tube, and which, in advanced condition of the mandrin, as shown in FIG. 11, is released again. The front end of the cannula tube 14 is not expandable by fluid pressure, which does not deform rod 31 of the mandrin 12 either. The connector 32 of the mandrin 12 is screwed on a thread 47 of the connector 15 of the retentive catheter 10, and from connector 32, the core 33 and the stiffening zone 33a extend in forward direction inside connector 15 where rod 31 joins the stiffening zone 33a. Intermediate core 33 and stiffening zone 33a, there is a sealing bead 48 sealing the liquid-receiving front portion of the connector 15 against the rear portion thereof. Connector 32 of the mandrin comprises a laterally projecting grip 49 by which the connector 32 may be rotated about the longitudinal axis of mandrin 12. If mandrin 12 is rotated about its longitudinal axis, it is displaced longitudinally by the thread 47, whereby valve 45 may be opened and closed. If fluid is injected or infused, the connector 32 is rotated by 90° about the longitudinal axis of shaft 31, whereby valve 45 is opened. Upon termination of the injection or infusion, the grip 49 is returned, whereby valve 45 is moved into the closing condition.

Figure 13:
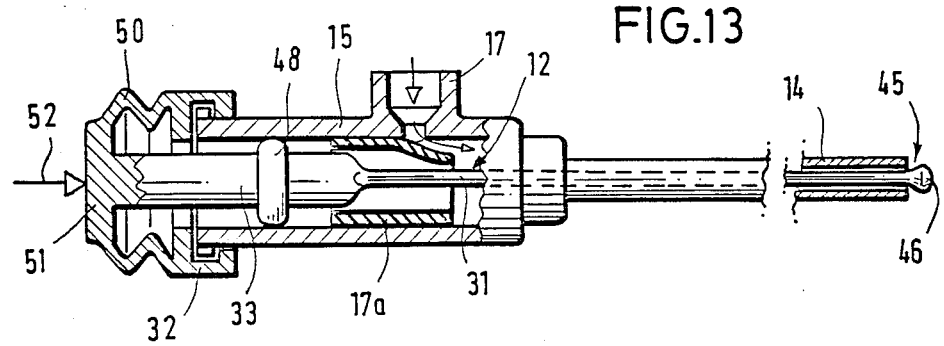
FIG. 13 shows a catheter device in which the mandrin is adjusted by axial pressure.

In FIG. 13, the connector 32 comprises a Luer-lock coupling to be secured to connector 15. Further, the connector 32 is provided with a flexible element 50 designed as a concertina bellow which, at its end wall, forms a pressure plate 51. Shaft 31 is connected thereto via core 33. The flexible element 50 normally draws shaft 31 into the return position in which the headpiece closes valve 45. By exerting an axial pressure against the pressure plate 51 in the direction of arrow 52, the mandrin 12 is urged into the advance position, whereby valve 45 is opened. If the pressure plate 51 is released, the valve 45 automatically takes again its closing position. FIG. 13 shows the hose portion 17a in pass position. Due to the fluid pressure, it is so deformed that the fluid may move from the injection port 17 into the cannula tube 14.

Figure 14:
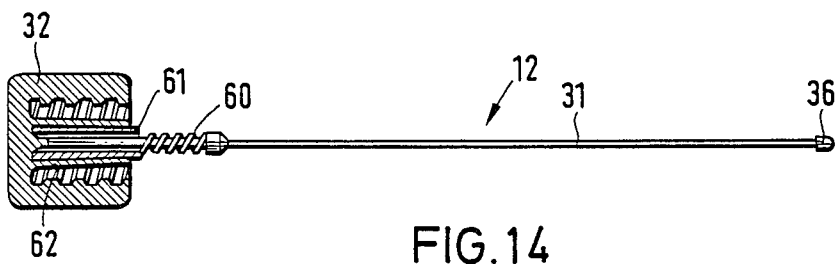
FIG. 14 is an embodiment of the mandrin comprising an integrated spring element.

Mandrin 12 of FIG. 14 comprises an elongated rod 31 with a headpiece 36. The rear end of the rod 36 is provided with a spring element 60 which is elastic in the longitudinal direction of the mandrin rod and which, in the instant embodiment, consists of a plastic or steel coil. The resilient element 60 is connected to a casing 61 secured in a sleeve 62 of the connector 32 which consists of a thread cap with internal thread to be screwed onto the connecting adapter 16 of the retentive catheter 10 (FIG. 1). The threaded sleeve overengaging the connecting adapter 16 acts also as a protection against contamination and avoids its penetration into the interior of the connector 15. A fluid pressure in the catheter tube 14 urges the headpiece 36 to the outside, whereby the resilient element 60 is expanded thus forming an outlet aperture at the front end of the catheter tube 14.

Figure 15:
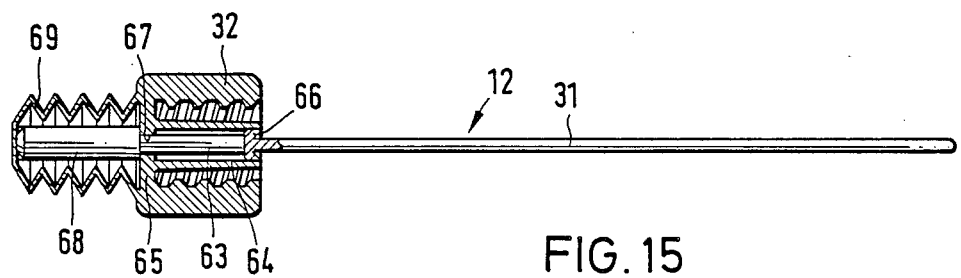
FIG. 15 is an embodiment of the mandrin having concertina bellow at its rear for the automatic withdrawal of mandrin rod.

Mandrin 12 of FIG. 15 contains an elongated mandrin rod 31 coacting, similar to FIG. 4, with a constriction at the front end of the catheter tube. A shaft 63 provided at the rear end of the mandrin rod 31 extends through a sleeve 64 which is coaxially positioned in the connector 32 designed as a screw cap (retaining nut) and projecting forwardly from the rear end wall 65. Shaft 63 comprises a piston 66 arranged in the transition between shaft 63 and mandrin rod 31 and being adapted to sealingly move along the cylindrical inner surface of the sleeve 64. Shaft 63 sealingly extends through an opening 67 in the end wall 65 and its rear end comprises a thicker portion 68 supported by the end wall 65, said thicker portion joined to connector 32 and acting as a spring on shaft 63 in order to advance mandrin 31. A fluid pressure in the catheter tube 14 (FIG. 1) acts on the piston 66 to drive shaft 63 counter to the spring action of the concertina bellow 69 in backward direction, while the valve at the front end of the catheter tube is opened accordingly. If the fluid pressure decreases, the concertina bellow 69 again drives shaft 63 and mandrin 31 into the front end position. The connector 32 is again designed as a retaining nut which, in particular also with its sleeve 64, forms an effective protection against contamination for the mandrin rod and the interior of the catheter tube.

Figure 16:
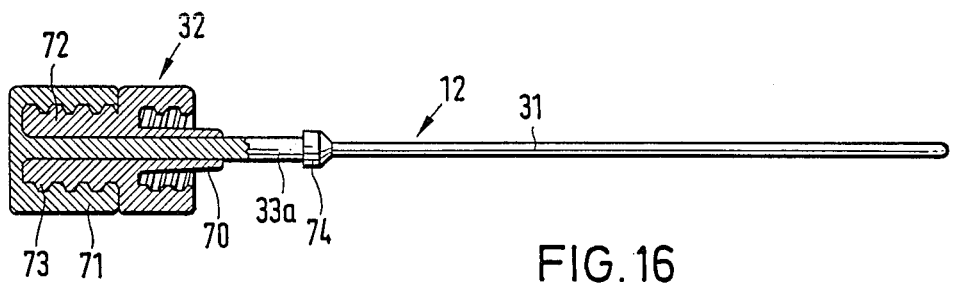
FIG. 16 is an embodiment of the mandrin in which the mandrin rod is withdrawn by turning left-hand a threaded cap for opening and FIG. 17 is an embodiment of the mandrin in which the mandrin rod is advanced by turning a threaded cap right-hand for opening the valve.

In case of FIG. 16, the rear end of the mandrin rod 31 contains a stiffening zone 33a extending slidingly through a sleeve 70 at connector 32 and having a screw cap 71 at the rear end. Said screw cap 71 is screwed onto a thread piece 72 projecting from the rear end of connector 32 and extending through the stiffening zone 33a.

The thread 73 is of the left-hand type thus allowing to withdraw by left-hand rotation of the screw cap 71 the mandrin rod 31 in order to pen the valve. The return movement is limited by a flange 74 of the mandrin rod which abuts against sleeve 70 before the screw cap 71 is unscrewed and removed from the thread piece 72. To close again the valve, the cap 71 is screwed again by right-hand rotation onto the thread piece 72. The screw cap 71 is a retaining nut. Due to this provision and to the fact that the stiffening zone 33a closely adjoins the channel of sleeve 70 and of the thread piece 72, contaminations of the mandrin are excluded.

Figure 17:
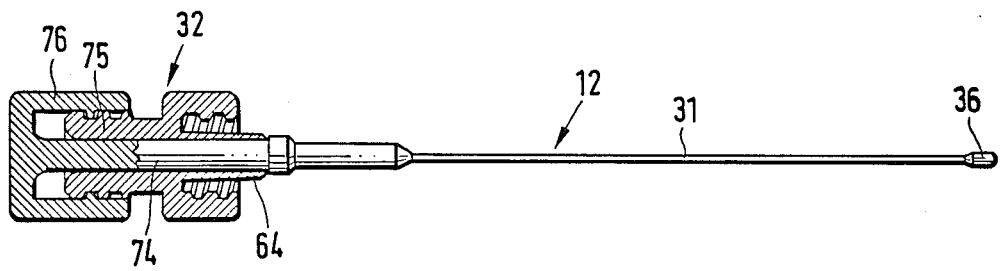

In the embodiment of FIG. 17, the front end of mandrin 31 is provided with a headpiece 36 which is a union-nut type screw cap. It comprises a sleeve 64 through which shaft 74 extends at the rear end of the mandrin rod 31, a hollow thread shaft 75 with external thread being formed integrally with the connector 32 for the passage of the shaft 74, the rear end of said shaft 74 being provided with a union-nut type screw cap 76 engaged by the thread of shaft 75. Said thread is of the left-hand type. By clockwise turning the union-nut-type screw cap 76, the mandrin rod 31 is advanced so that the headpiece 36 exits from the catheter tube and the valve is opened. By an anticlockwise rotation of the union-nut-type screw cap 76, the valve is closed.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A catheter device comprising:
   a retentive catheter including a cannula tube having a first end and a second end,
   a connecting means including a lateral injection port adjacent the first end of the cannula tube,
   a mandrin insertable through the connector into the catheter for blocking blood inflow into the second end of the cannula tube, said mandrin sealingly secured to said connector means,
   the mandrin and the cannula tube being mutually configured to define therebetween a substantially longitudinal fluid channel extending substantially between the injection port and the second end of the cannula tube, and
   a valve formed by the mandrin and the cannula tube adjacent the second end of the cannula tube.

2. A catheter device comprising:
   a retentive catheter including a cannula tube having a first end and a second end,
   a connector means including a lateral injection port adjacent the first end of the cannula tube,
   a mandrin insertable through the connector into the catheter for blocking blood inflow into the second end of the cannula tube, said mandrin sealingly secured to said connector means,
   the mandrin being configured to define therein a substantially longitudinal fluid channel extending substantially between the injection part and the second end of the cannula tube, and
   a non-return valve provided in the mandrin adjacent the second end of the cannula tube, the valve being openable upon overpressure within the mandrin.

3. A catheter device as defined in claim 1 or 2 further comprising
   displacement means for longitudinally displacing the mandrin relative to the cannula tube to thereby open and close the valve.

4. A catheter device as defined in claim 3 wherein the displacement means comprises
   threaded engagement means provided between the mandrin and the connector for translating relative rotation between the mandrin and the connector into longitudinal displacement of the mandrin relative to the cannula.

5. A catheter device as defined in claim 3, further comprising an axially flexible, resilient biasing means joining the mandrin and the connector for biasing the valve in a closed position.

6. A catheter device comprising:
   a catheter including a cannula tube having a first end and a second end,
   a connector means including a lateral injection port adjacent the first end of the cannula tube,
   a mandrin insertable through the connector into the catheter for blocking blood inflow into the second end of the cannula tube, said mandrin sealingly secured to said connector means,
   the mandrin and the cannula tube being mutually configured to define therebetween a substantially longitudinal fluid channel extending substantially between the injection port and the second end of the cannula tube, and
   a valve formed by the mandrin and the cannula tube adjacent the second end of the cannula tube adjacent the second end of the cannula tube, wherein the valve is a nonreturn valve which is opened in the case of overpressure in the longitudinal fluid channel.

7. A catheter device as defined in claim 6, wherein the nonreturn valve comprises a flexibly expandable constricted portion of the cannula tube configured to embrace the mandrin.

8. A catheter device as defined in claim 6, wherein the nonreturn valve comprises:
   a headpiece, disposed adjacent one end of the mandrin, the headpiece having a cross section greater than that of the mandrin, and
   a flexibly expandable portion of the cannula tube configured to embrace the headpiece.

9. A catheter device as defined in claim 6, wherein the nonreturn valve comprises:
   a headpiece provided adjacent one end of the mandrin for blocking the longitudinal fluid channel, and
   means for removing the headpiece from the cannula tube in case of overpressure in the longitudinal fluid channel.

10. A catheter device as defined in claim 8 or 9, wherein
    the mandrin includes a substantially round cross section defining an exterior diameter,
    the cannula tube defines an interior diameter, and
    at least a portion of the exterior diameter of the mandrin is smaller than the interior diameter of the cannula tube.

11. A catheter device as defined in claim 8 or 9, wherein the longitudinal fluid channel comprises at least one longitudinal groove in the mandrin.

12. A catheter device as defined in claim 9, wherein the mandrin comprises a helical coil forming a helical fluid channel, the helical coil being axially expandable in the case of overpressure in the longitudinal fluid channel.

* * * * *